United States Patent [19]
Kassman

[11] Patent Number: 5,549,196
[45] Date of Patent: Aug. 27, 1996

[54] CONDOM APPLICATOR AND PACKAGING

[76] Inventor: Leon B. Kassman, 245 E. 24th St., New York, N.Y. 10010

[21] Appl. No.: 391,440
[22] Filed: Feb. 21, 1995
[51] Int. Cl.⁶ .............................. B65D 85/08; A61F 6/04
[52] U.S. Cl. ............................ 206/69; 128/844; 604/349
[58] Field of Search .............................. 128/844; 206/69; 604/349

[56] References Cited

U.S. PATENT DOCUMENTS

| | | | |
|---|---|---|---|
| 4,289,232 | 9/1981 | Seibel et al. | 206/69 |
| 4,840,187 | 6/1989 | Brazier | 206/69 |
| 4,961,734 | 10/1990 | Kassman | 206/69 |
| 5,170,887 | 12/1992 | Potts et al. | 206/69 |
| 5,205,298 | 4/1993 | Hurst | 128/844 |
| 5,238,103 | 8/1993 | Swisher | 206/69 |
| 5,437,286 | 8/1995 | Stratton | 206/69 |

Primary Examiner—Jimmy G. Foster
Attorney, Agent, or Firm—Abelman, Frayne & Schwab

[57] ABSTRACT

A packaging for a condom includes an applicator having a memory of its original shape, which is secured in compressed condition within a cap member, and which is manually releasable from said confinement within said cap member to permit axial extension of the applicator under the influence of its stored memory.

10 Claims, 5 Drawing Sheets

CONDOM APPLICATOR AND PACKAGING

FIELD OF THE INVENTION

This invention relates to an applicator for a condom and to the applicator of the invention when packaged in conjunction with a condom for sale as a pre-assembled unit.

BACKGROUND OF THE INVENTION

Condoms are well-known in the art, and essentially are comprised of a thin tubular film of a readily expandable material, commonly latex or a plastisol, which has been formed with an impervious end closure, the tubular portion of the condom having been rolled to provide a relatively stable ring.

The application of the condom can be troublesome and type-consuming owing to the flexibility and compliance of the condom in its rolled form, and, the tendency of the condom to become unrolled before it is properly applied.

Collapsible and axially expandable tubes and bottles are well-known in the art for use as construction toys, or, for the storage of foods or chemicals. U.S. Pat. No. 3,908,704 teaches such expandable and collapsible tubular constructions.

U.S. Pat. No. 4,961,734 teaches the use of such an expandable and collapsible tube in combination with a condom for use as a condom applicator.

That applicator, while providing admirably for the extension of a condom under sub-atmospheric pressure, as generated within the applicator upon extension of the applicator from a collapsed condition to an extended condition, is somewhat cumbersome, in that it requires the applicator to be grasped using two hands, and then expanded axially by use of manual force.

Preferred would be an applicator for a condom that automatically extends itself upon opening of the packaging within which the device is stored and offered for sale.

SUMMARY OF THE INVENTION

It is an object of this invention to provide an applicator for use in conjunction with a conventional condom to facilitate the application of the condom, and which, additionally, is capable of moving from a retracted to an extended position when released from a stored axially compressed condition.

It is also and object of this invention to provide a combined condom and applicator assembly as a complete unit which can be pre-packaged for sale at a point of retail.

Further it is an object of this invention to provide an applicator and condom as a prepackaged unit that is relatively unobvious, and which readily can be stored in a ladies purse or handbag, the pre-packaged unit simulating in appearance a ladies powder compact, or, a container of the type commonly employed for the packaging of cosmetics, such as face creams and the like.

It is also an object of this invention to provide an applicator for a condom that can be carried unobtrusively in a persons pocket, and which simulates in general shape the shape of a container used for the packaging of candy drops, throat lozenges and the like.

According to the present invention, contrary to the prior teachings in Kasman U.S. Pat. No. 4,961,734, the applicator, instead of being a device that is to be manually extended, it is formed as an axially-extendable tube having an inherent memory of its original shape and configuration.

Following the teachings of Kasman U.S. Pat. No. 4,961,734, the condom is stored within the applicator while the applicator is in a collapsed condition, and is moved into the expanded and extended condition by sub-atmospheric pressure existing within the applicator at the time the applicator expands to its extended condition.

Means are provided for forcibly holding the applicator in its contracted position for storage and transportation of the device, which, upon removal of a threaded cap or the rupturing of a tear-off tab releases the applicator from the constraining force acting to hold the applicator in a contracted position, the applicator then being free to return to its extended original shape under the influence of the inherent memory of the material from which the applicator is formed.

As in Kasman U.S. Pat. No. 4,961,734, a condom is positioned within the collapsed axially-extendable tube comprising the applicator, and, the open end of the condom is detachably attached to a ring-shaped flange in a hematically sealed manner with a portion of the condom positioned in close proximity to the inner wall of the collapsed container.

Further, it is an object of this invention that to make it difficult to re-load the applicator with a fresh condom after initial use of the applicator, the object here being to prevent cross-infection due to the use of an improperly cleansed or sterilized applicator.

As has been previously proposed, the applicator itself can be charged with a quantity of lubricant, or spermicide, or other medication effective to prevent the transmission of sexually transmitted disease.

DESCRIPTION OF THE DRAWINGS

The invention will now be described with reference to the accompanying drawings, which illustrate preferred embodiments of the invention, and in which.

DESCRIPTION OF THE PREFERRED EMBODIMENTS

Figure 1:
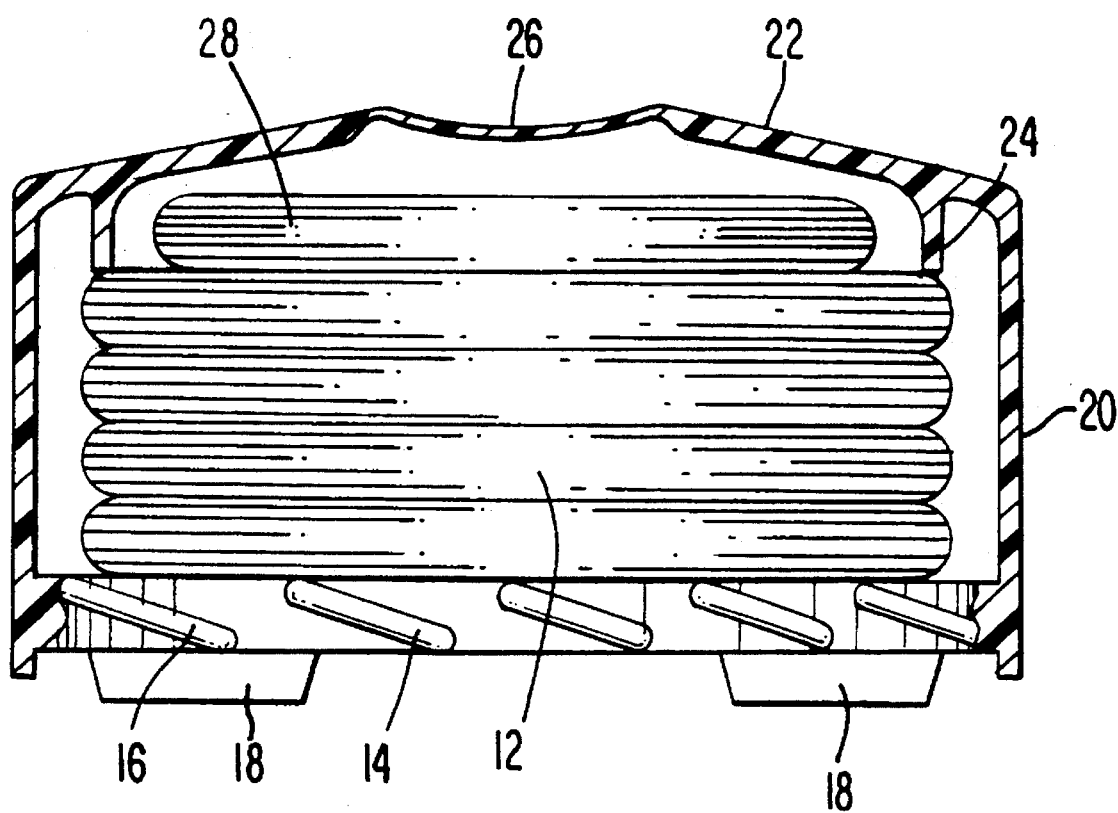
FIG. 1 illustrates one preferred embodiment of the present invention, shown when in a contracted position for storage and transportation.

FIG. 1 of the drawings illustrates one preferred embodiment of the invention, shown in the condition in which the applicator is packaged for sale at a point of retail.

Figure 2:
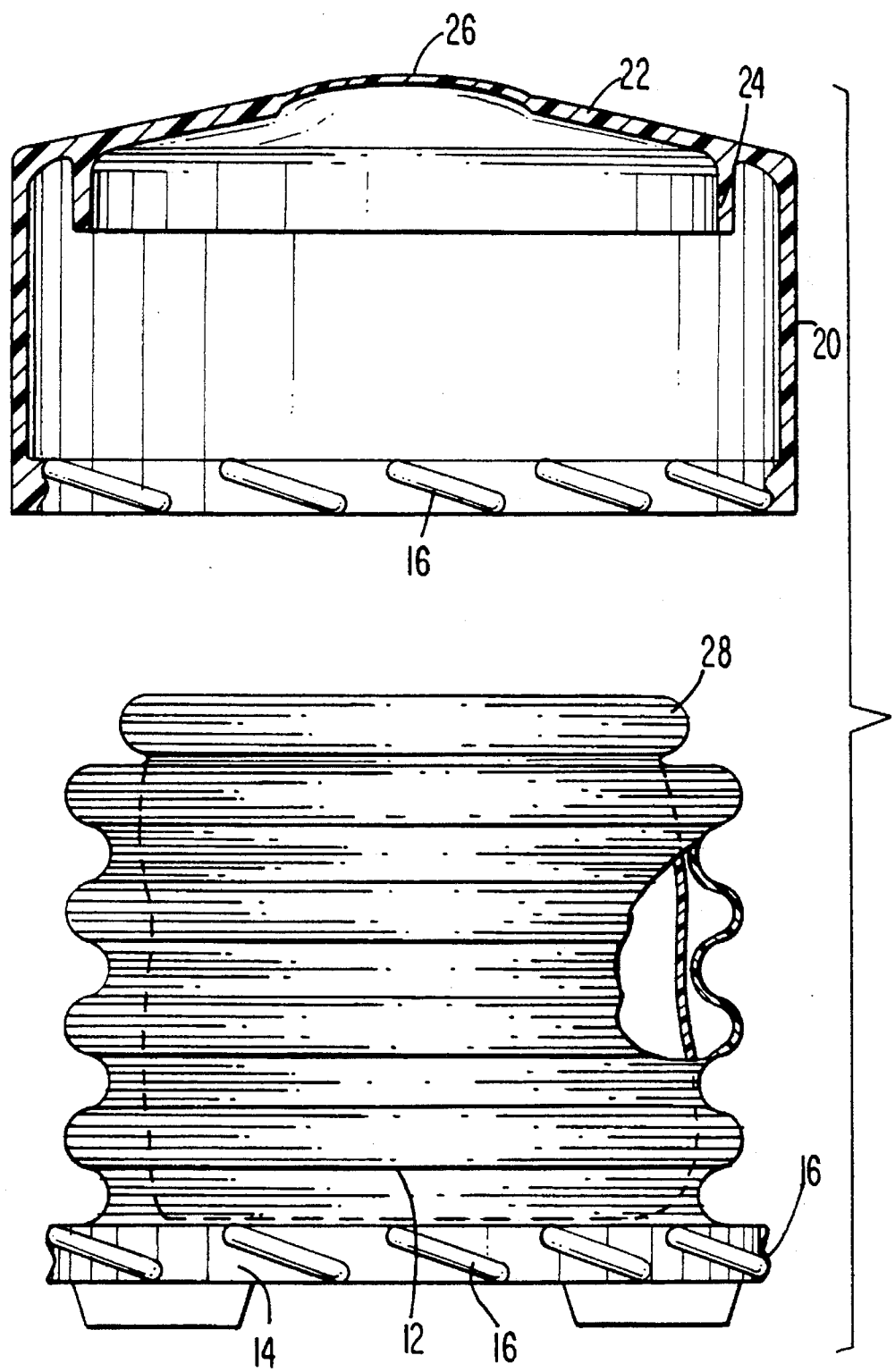
FIG. 2 is an exploded view of a cap and an applicator as shown in FIG. 1, when the cap has been removed from the applicator.

The applicator itself is indicated at 12, and is comprised of an axially corrugated tube that is capable of being compressed from an initial axial length, for example, as illustrated in FIG. 2, to a contracted axial length, for example, as illustrated in FIG. 1.

The applicator 12 includes a bottom wall 14 providing an end closure for the applicator, the end wall 14, as illustrated, being provided with a screw thread 16, which preferably is a quick start screw thread, which is threadedly received within an open end of a cap 20, the free edge of the cap being provided with corresponding threads for cooperation with the screw thread 16.

The cap 20, at its upper edge, proceeds into an end closure 22 of the cap, the cap having internally thereof an annular rib 24 dimensioned to engage and compressively hold the applicator 12 in a compressed condition at a position spaced radially outwards of a contained rolled condom.

Preferably the cap is provided with a pop-diaphragm portion 26, which, if the device is in an unopened and pristine condition in which the interior of the device is under sub-atmospheric pressure, extends concavely inwards, and which, at the time the cap and applicator are separated from each other then moves to an outwardly convex position as illustrated in FIG. 2.

Preferably, a semi-adhesive is used as a sealant between the threads of the applicator 12 and those of the cap 20 in order to preserve a hematic seal within the packaging.

A rolled condom 28, as more clearly illustrated in FIG. 2 is positioned over an axially extending tubular lip of the applicator, and, is loosely confined within the body of the applicator.

Referring now to FIG. 2, when the cap 20 is removed from the applicator, the threads 16 are disconnected, and, the annular rib 24 is moved out of compressive engagement with the opposite end of the applicator 12. The applicator is then free to expand axially under its own inherent memory, this in turn acting to extend the body of the condom 28 contained within the applicator. Extension of the applicator generates a negative pressure between the inner wall of the applicator and the outer surface of the condom acting to expand the body of the condom radially outwardly, and also longitudinally.

Figure 3:
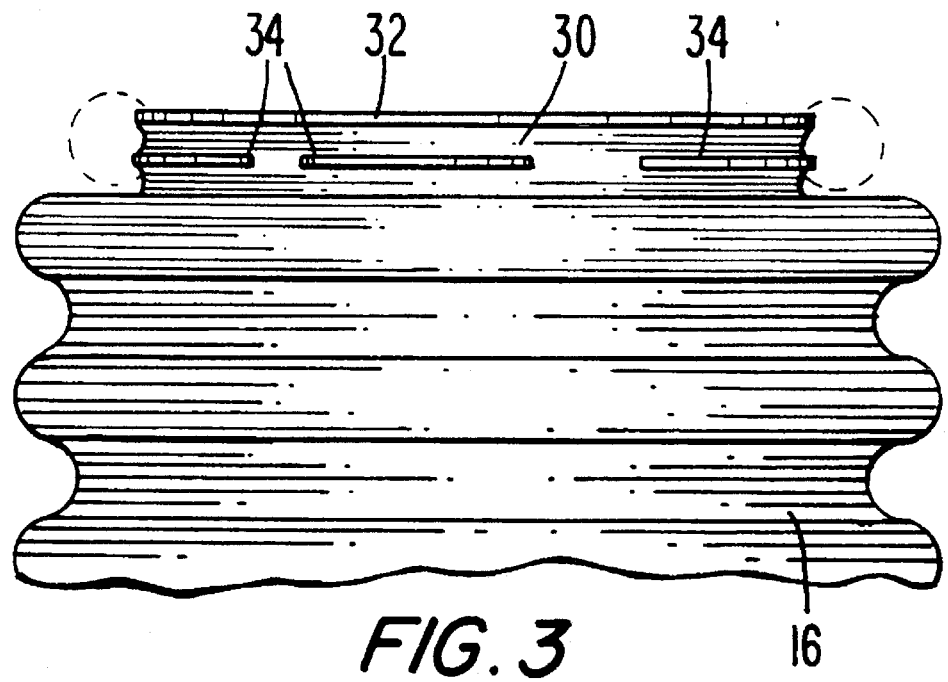
FIG. 3 illustrates a lip of the applicator which provides a seating for a rolled condom.

Preferably, and as illustrated in FIG. 3, the applicator is provided with a tubular neck 30 providing a seating for the rolled portion of the condom, the condom preferably being supported by an annular flange 32 at the free edge of the tubular neck 30, and, by arcuate ribs 34 spaced axially from the annular flange 32, this permitting ready gripping of the rolled condom for its removal from the applicator.

As illustrated in FIGS. 1, 2 and 3, the body of the applicator is of axially corrugated or sinusoidal form, such as readily can be produced by blow-molding.

Figure 4:
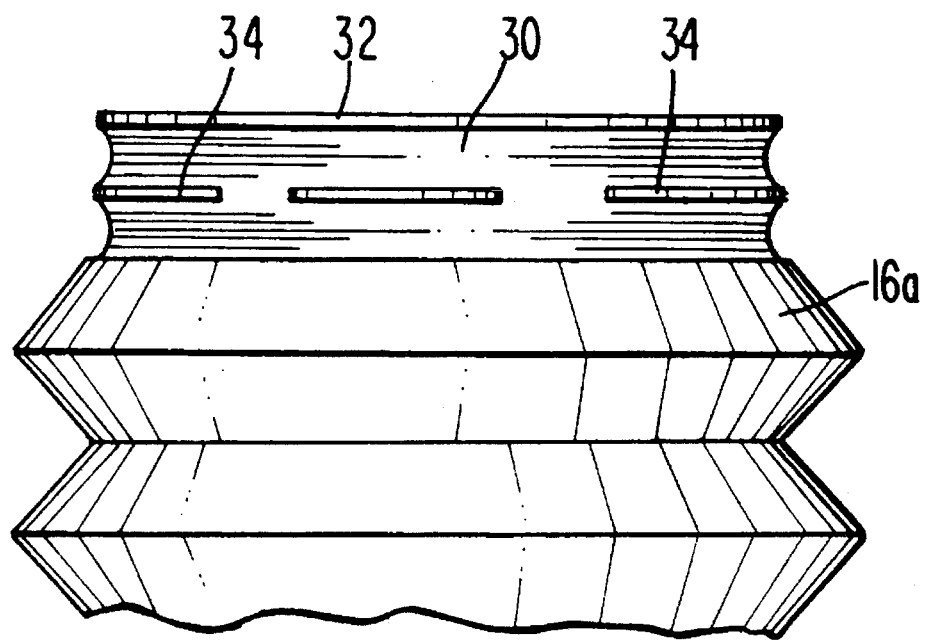
FIG. 4 illustrates an alternative form of the applicator.

Alternatively, and as illustrated in FIG. 4, the body of the applicator can be of concertina form, as illustrated at 16a in FIG. 4, in which the axial wall of the applicator is defined by interconnected oppositely inclined annular rings.

In all instances, the applicator is formed from a material having an inherent memory of its original shape, in order that, when released from compression by the cap 20, the body of the applicator will elongate and resume its initial shape prior to compression. Numerous materials are known that possess this property, including plastics materials, such as P.V.C., such materials being readily formable by a molding process.

Figure 5:
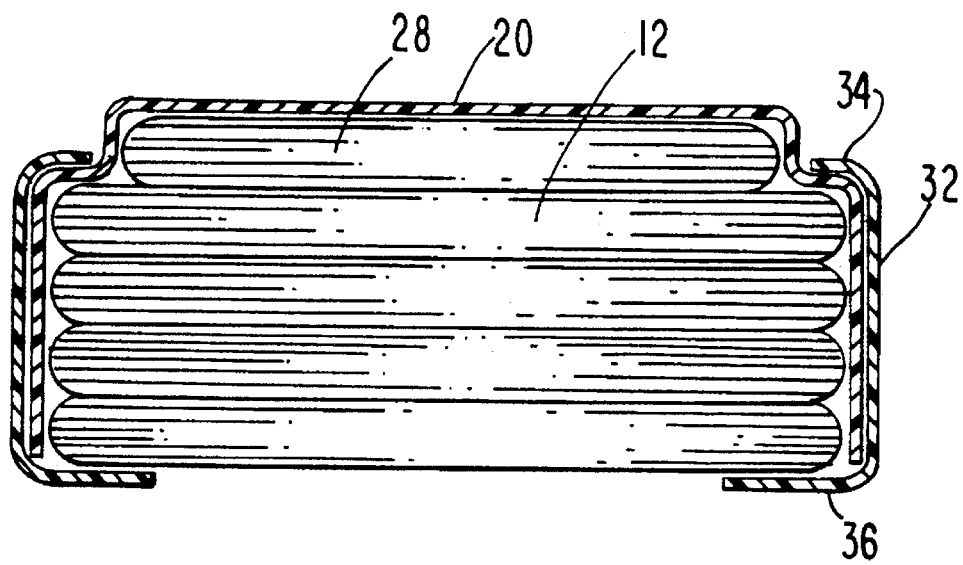
FIG. 5 illustrates an alternative form of the device of FIG. 1.

An alternative preferred construction is illustrated in FIG. 5, which similarly includes a cap 20 which has been forced into compressive surrounding relation with the applicator 12, subsequent to which a ring-shaped band of thermo shrinkable material 32 is placed in surrounding relation with the applicator 12 and cap 20, and is then heat shrunk to cause the axial extremities 34 and 36 to move radially inwardly into gripping relation with the cap 20 an the lower face of the applicator 12.

Figure 6:
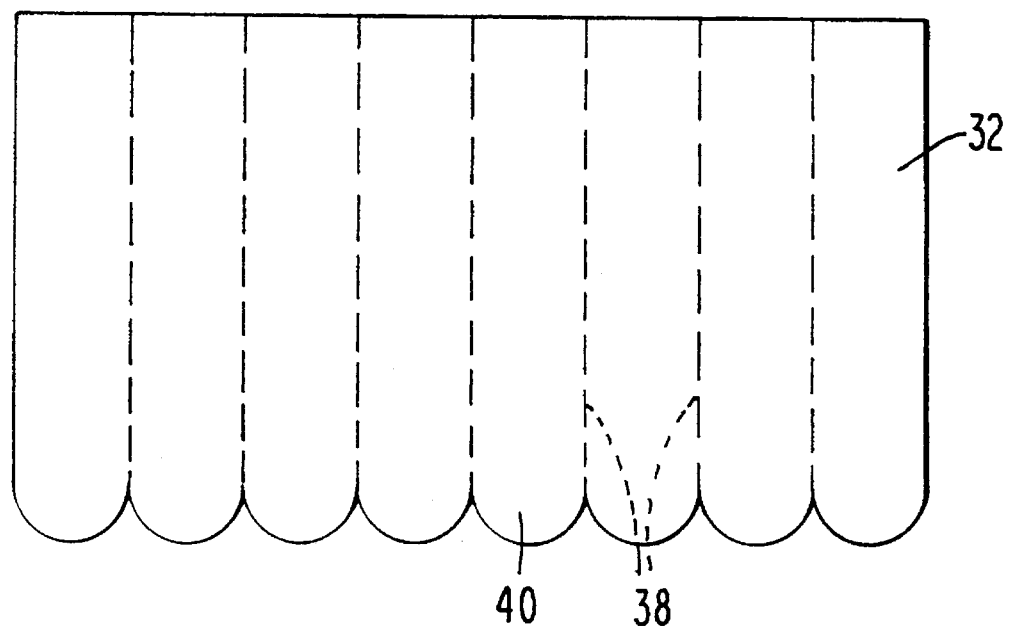
FIG. 6 illustrates a form of shrink wrap that can employed in the assembly of the device of the FIG. 5; and, FIG. 7 shows and alternative form of the applicator.

Preferably, and as illustrated in FIG. 6, the shrink wrap 32 is axially perforated at 38 to provide tear lines extending axially of the shrink wrap 32, and, preferably is provided at its lower edge with tabs 40 that permit easy gripping of the shrink wrap, and its axial tearing along one of the perforated lines 38.

So doing will release the compressive engagement of the shrink wrap 32 with the cap 20 and the end face of the applicator 12, this permitting the applicator to expand axially, and permitting the cap 20 to be discarded.

Figure 7:
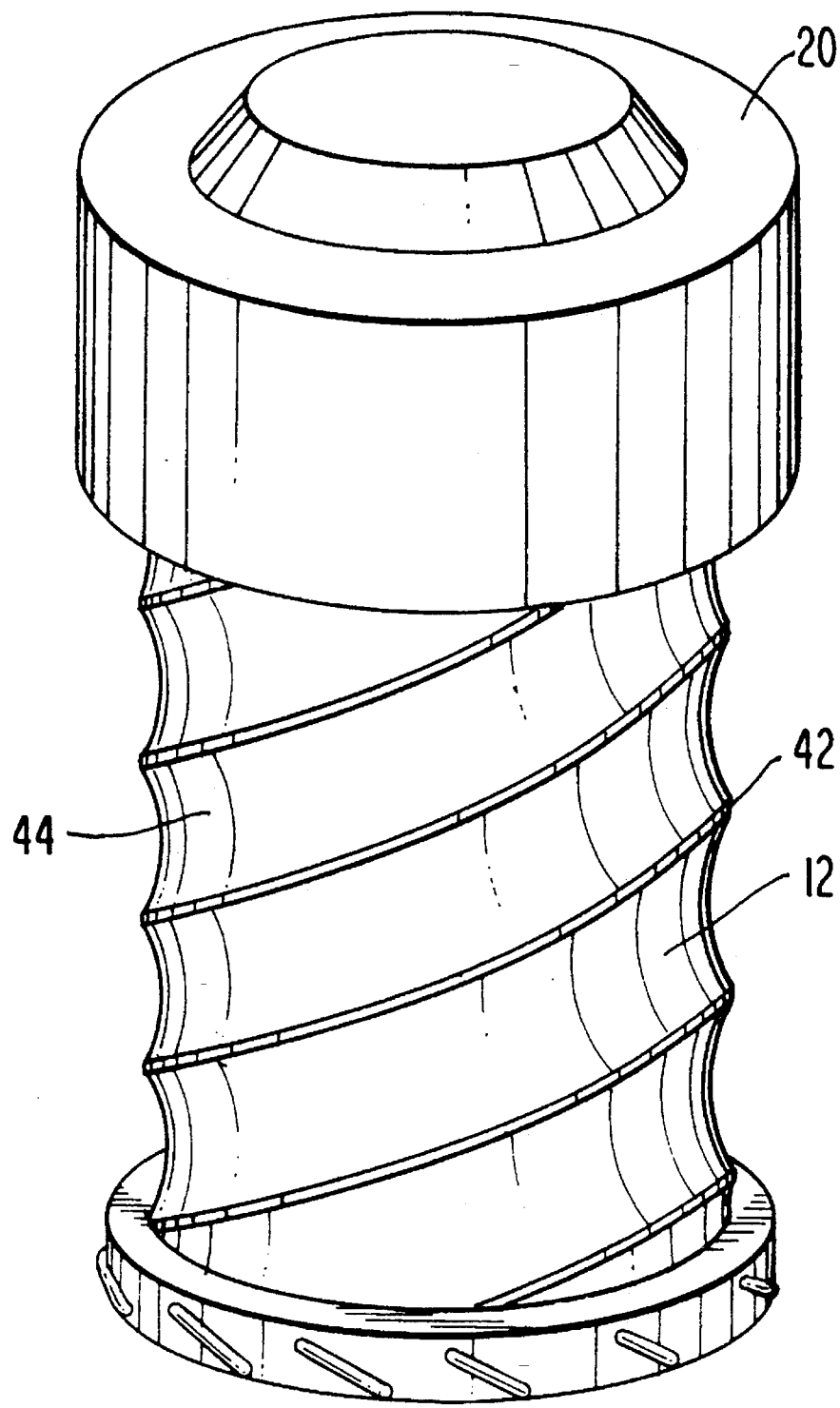

Other configurations of cap will be apparent to those skilled in the art, as will be other configurations of the axially extendible applicator 12. For example, and as illustrated in FIG. 7, the applicator 12 can be molded in surrounding relation with a spiral spring 42, the convolutions of which are encased in a continuous flexible web 44 extending between the convolutions of the spring 40.

Reloading of a condom within the applicator 16, in the absence of the required jig, requires very considerable manual dexterity, and in most cases will defeat attempts in that respect. Not only must the applicator be held in the compressed retracted position but also, a rolled condom must at the same time be stretched and positioned over the tubular neck 30 of the applicator. In the alternative, the rolled condom must first be positioned over the neck of the applicator, and then be stretched at at least one position in a direction radially outwards of the neck to provide an air exhaust passage for air exiting the applicator during the compression and retraction thereof.

I claim:

1. A condom applicator and packaging, comprised by:

a tubular member formed of a resilient flexible material having a memory of its original shape, said tubular member including an axial tubular wall, an end wall providing a closure for one end of said tubular wall, and, a ring-shaped neck at an opposite end of said tubular wall of lesser diameter than said tubular wall;

a cup-shaped member having a closed end and a skirt having a free edge positioned over said tubular member;

means securing said tubular member within said cup-shaped cap member in an axially compressed condition of said tubular member;

said means being manually releasable to permit removal of said cap member from said tubular member, and, permit axial expansion of said tubular member towards its original shape under the stored inherent memory of the material comprising said tubular member.

2. The condom applicator and packaging of claim 1, in which said securing means comprised interfitting threads on an interior surface of said free edge of said cap, and complimentary threads formed on an outer perimeter of said end wall of said closure.

3. The condom applicator and packaging of claim 1, including ridges on said bottom wall of said tubular member facilitating manual relative rotation between said cap and said tubular member.

4. The condom applicator and packaging of claim 1, in which said cap includes an internal annular rib engageable with an end wall of said tubular member at a position spaced radially outwardly of a tubular neck of said tubular member.

5. The condom applicator and packaging of claim 1, in which said securing means is provided by a ring-shaped band of heat shrinkable material that has been shrunk into compressive engagement with an external surface of said cap, and which extends radially inwardly of said free edge of said cap and said end wall of said tubular member, whereby to confine a compressed said tubular member within the confines of said cap.

6. The condom applicator and packaging of claim 5, in which said ring-shaped band is axially perforated.

7. The condom applicator and packaging of claim 6, in which one edge of said ring-shaped band is provided with tabs permitting tearing of said ring-shaped band along at least one of said lines of perforation.

8. The condom applicator and packaging of claim 1, in which said axial tubular wall of tubular body is axially sinusoidal and provides circumferentially extending corrugations of said axial tubular wall.

9. The condom applicator and packaging of claim 1, in which said axial tubular wall of tubular member is formed of adjoining interconnected frusto-conical rings arranged in a saw-tooth configuration.

10. The condom applicator and packaging of claim 1, in which said axial tubular wall of said tubular member is in the form of a compression spring, adjacent turns of said compression spring being interconnected one with the other by a web of lesser resistance to deformation than said turns of said compression spring.

* * * * *